(12) United States Patent
Cundiff et al.

(10) Patent No.: US 10,898,248 B2
(45) Date of Patent: Jan. 26, 2021

(54) ORTHOPEDIC IMPLANT ASSEMBLIES AND DEVICES

(71) Applicant: Fusion Orthopedics, LLC, Mesa, AZ (US)

(72) Inventors: Adam J. Cundiff, Gilbert, AZ (US); Nathan G. Peterson, Gilbert, AZ (US)

( * ) Notice: Subject to any disclaimer, the term of this patent is extended or adjusted under 35 U.S.C. 154(b) by 6 days.

(21) Appl. No.: 16/510,799

(22) Filed: Jul. 12, 2019

(65) Prior Publication Data

US 2019/0336189 A1 Nov. 7, 2019

Related U.S. Application Data

(63) Continuation-in-part of application No. 15/663,173, filed on Jul. 28, 2017, now abandoned.

(51) Int. Cl.
*A61B 17/04* (2006.01)
*A61B 17/86* (2006.01)
*A61F 2/08* (2006.01)
*A61B 17/84* (2006.01)
*A61B 17/68* (2006.01)
*A61F 2/30* (2006.01)

(52) U.S. Cl.
CPC ........ *A61B 17/8605* (2013.01); *A61B 17/686* (2013.01); *A61B 17/846* (2013.01); *A61B 17/8685* (2013.01); *A61F 2/30* (2013.01); *A61B 2017/8655* (2013.01); *A61F 2002/30622* (2013.01)

(58) Field of Classification Search
CPC combination set(s) only.
See application file for complete search history.

(56) References Cited

U.S. PATENT DOCUMENTS

| 8,303,589 | B2 | 11/2012 | Tyber | |
|---|---|---|---|---|
| 8,313,487 | B2 | 11/2012 | Tyber | |
| 8,328,806 | B2 | 12/2012 | Tyber | |
| 8,343,199 | B2 | 1/2013 | Tyber | |
| 8,900,274 | B2 | 12/2014 | Tyber | |
| 8,920,453 | B2 | 12/2014 | Tyber | |
| 8,920,476 | B2 | 12/2014 | Tyber | |
| 9,017,329 | B2 | 4/2015 | Tyber | |
| 9,044,282 | B2 | 6/2015 | Tyber | |
| 9,289,220 | B2 * | 3/2016 | Wolfe | ............... A61B 17/1717 |
| 9,364,271 | B2 | 6/2016 | Tyber | |
| 9,615,870 | B2 | 4/2017 | Tyber | |
| 2010/0121325 | A1 | 5/2010 | Tyber | |

(Continued)

*Primary Examiner* — Sameh R Boles

(57) ABSTRACT

Innovative orthopedic implant assemblies and devices are provided. One example assembly may include two implant devices. An example implant device may include two ends oppositely located with a bulbous portion at one end. An example bulbous portion may include a crown defining a terminal axis of one end and a thread disposed on an exterior surface of the bulbous portion and originating at the crown. A threaded portion defining a second terminal axis may be located at another end. An example second implant device may include two ends oppositely located. A looped portion defining an aperture including an interior surface with a groove disposed therein may be located at one end and the other end may include a screw portion or a nail portion. The thread and the groove can lock the bulbous portion and the looped portion when engaged with one another.

20 Claims, 8 Drawing Sheets

(56) References Cited

U.S. PATENT DOCUMENTS

2011/0125153 A1  5/2011  Tyber
2011/0230884 A1  9/2011  Tyber
2015/0173811 A1  6/2015  Tyber
2016/0278823 A1  9/2016  Tyber

* cited by examiner

ORTHOPEDIC IMPLANT ASSEMBLIES AND DEVICES

REFERENCE TO RELATED APPLICATION

This application is a Continuation-In-Part of and claims priority to U.S. patent application Ser. No. 15/663,173 filed on Jul. 28, 2017, the contents of which are incorporated herein by reference in their entirety.

BACKGROUND

Field of the Technology

The present technology relates generally to systems and apparatus for fusing bones and joints, and more particularly to, orthopedic implant assemblies and devices.

Description of the Related Art

Intraosseous fixation differs from traditional fixation devices in that hardware is not typically left exposed to soft tissue. As a newer form of fixation in, for example foot and ankle arthrodesis surgery, previous implant assemblies and/or devices require precise instrumentation that can be difficult to use. If an implant assembly/device and its associated instrumentation are not properly aligned, it can be difficult to produce desirable results. For instance, intra-operative problems can occur when bone fragments, soft tissue, and imposing tendons create improper alignment both for an implant assembly/device itself and from the implant assembly/device to instnimentation, which can lead to a lack of compression, weak compression, and/or complete misalignment. These problems can be exacerbated through patient non-compliance, movement, and/or osteoporotic bone quality, etc., each of can result in a disengagement of a proper fitment of the implant assembly/device. Further, soft tissue aggravation and/or non-unions often occur as components in an implant assembly disengage and implant device(s) constructs become loose rather than tight. Accordingly, previous implant assemblies and implant devices are not as efficient and/or reliable as they otherwise could be.

SUMMARY

Various embodiments provide innovative orthopedic implant assemblies and devices. An example implant assembly may comprise a first implant device and a second implant device. A first implant device may include a first end and a second end oppositely located along a longitudinal first axis and a bulbous portion at the first end that extends along the first axis. An example bulbous portion may comprise a crown defining a first terminal axis of the first end and a thread disposed on an exterior surface of the bulbous portion and originating at the crown. A first threaded portion that extends along the first axis and defining a second terminal axis may be located at the second end. An example second implant device may include a third end and a fourth end oppositely located along a longitudinal second axis and a looped portion defining an aperture at the third end and including an interior surface with a groove disposed therein. In various embodiments, the thread and the groove lock the bulbous portion and the looped portion when engaged with one another.

In various embodiments, the thread may be a single-thread and/or the groove may be a single-groove. In some embodiments, the thread may rotate 360 degrees around the bulbous portion along the first axis and/or the groove may rotate 360 degrees around the looped portion. In further embodiments, the thread may rotate less than 360 degrees around the bulbous portion along the first axis and/or the groove may rotate less than 360 degrees around the looped portion.

The looped portion defining the aperture, in various embodiments, may provide an insertion side and an exit side for the first implant device. In some embodiments, the groove may terminate at the exit side. In further embodiments, the groove may originate at the insertion side. The looped portion, in additional embodiments, may define a fourth terminal axis.

An example implant device may comprise a first end and a second end oppositely located along a longitudinal axis, a bulbous portion at the first end that extends along the longitudinal axis, and a threaded portion at the second end that extends along the longitudinal axis and defining a second terminal axis. The bulbous portion, in some embodiments, may comprise a crown defining a first terminal axis of the first end and a thread disposed on an exterior surface of the bulbous portion and originating at the crown. In various embodiments, the threaded portion may be configured for implant in a bone and/or the thread may be configured to engage with a groove of an external implant device to lock the bulbous portion and the external implant device with one another.

In various embodiments, the thread may be a single-thread. In some embodiments, the thread may rotate less than or equal to 360 degrees around the bulbous portion along the longitudinal axis.

A further example implant device may comprise a first end and a second end oppositely located along a longitudinal axis and a looped portion defining an aperture at a first terminal axis of the first end and including an interior surface with a groove disposed therein. In various embodiments, the implant device includes a nail portion or a screw portion at the second end that extends along the longitudinal axis and defining a second terminal axis of the second end. The nail portion and the screw portion are configured to implant in a bone and/or the groove may be configured to engage with a thread of an external implant device to lock the looped portion and the external implant device with one another.

In various embodiments, the groove may be a single-groove. In some embodiments, the groove may rotate less than or equal to 360 degrees around the interior surface of the looped portion defining the aperture.

BRIEF DESCRIPTION OF THE DRAWINGS

The present disclosure is illustrated by way of example, and not by way of limitation, in the figures of the accompanying drawings in which like reference numerals are used to refer to similar elements.

DETAILED DESCRIPTION OF THE DRAWINGS

The innovative technology disclosed herein includes various aspects, such as orthopedic implant devices and assemblies for fusing bones and joints. The disclosed technology provides is advantageously more efficient and/or more reliable than previous implant devices and/or assemblies. It should be understood that language used in the present disclosure has been principally selected for readability and instructional purposes, and not to limit the scope of the subject matter disclosed herein.

Various embodiments may provide a locking feature that can ensure proper fitment to reduce implant impedance and/or poor surgical outcomes regardless of an implant environment. Some implant devices may utilize a Morse-taper fitment along with an interference thread on a crown that can aid instruments and interfacing screws in aligning and properly implanting of assemblies and devices. An interference thread can allow instruments to lock in conjunction with the taper to further ensure that an assembly/implant is properly aligned. Furthermore, the interference thread may aid in locking the screw compression in place and reducing the chance of an implant device from backing out over time.

Figure 1:
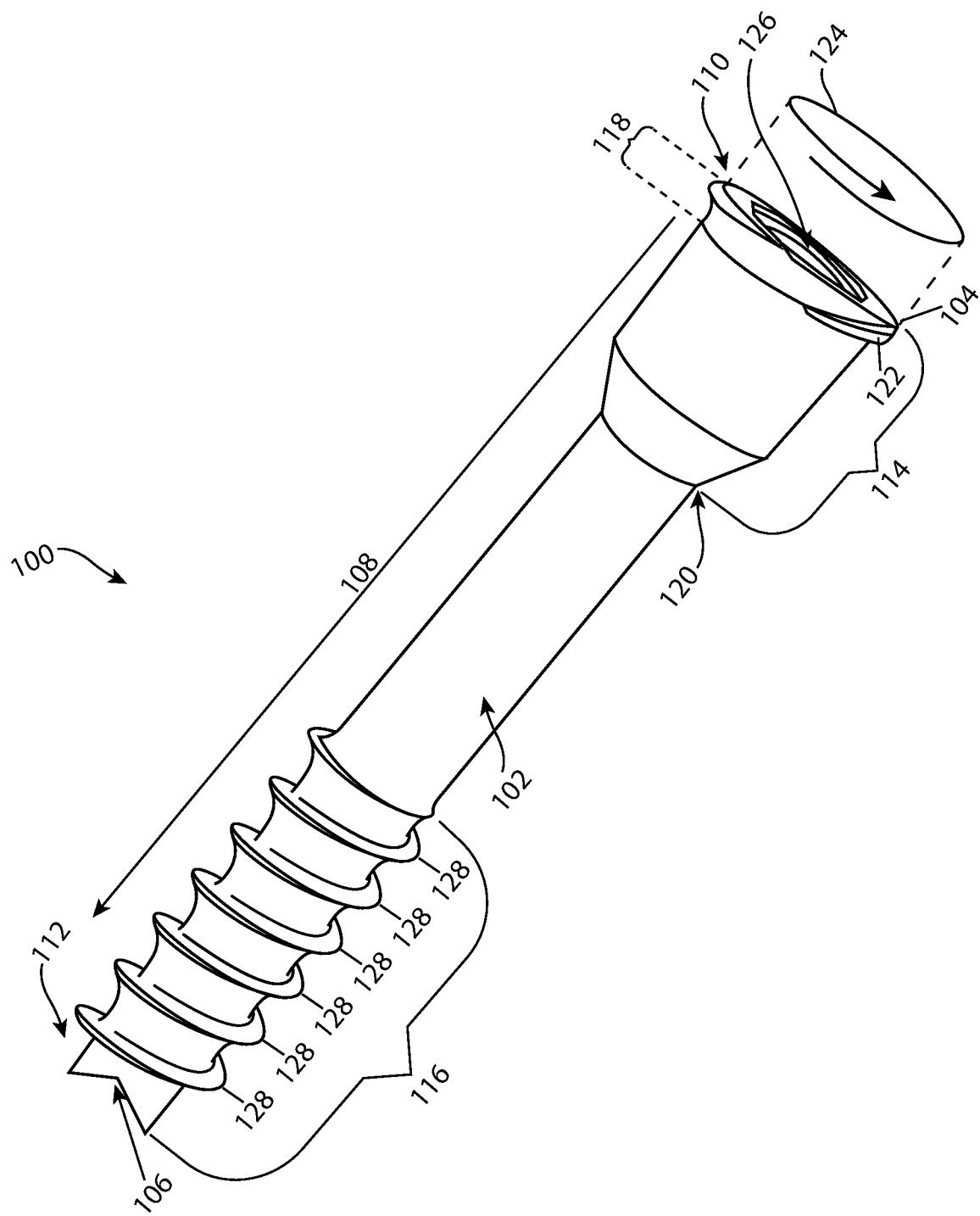
FIG. 1 is a diagram illustrating one embodiment of an implant device.

With reference now to the figures, FIG. 1 is a diagram illustrating an example implant device 100 in accordance with various embodiments. Implant device 100 may include a shaft portion 102 with a first end 104 and a second end 106 that are opposite one another along a longitudinal axis 108 and define a first terminal axis 110 and a second terminal axis 112, respectively. As shown, the implant device 100 may comprise, among other features, a bulbous portion 114 at the first end 104 and a screw portion 116 at the second end 106. Although the various embodiments may be referred to herein as an implant device 100, at least some embodiments of the implant device 100 may be considered and/or referred to as a lag screw.

The bulbous portion 114, in various embodiments, may originate at the first terminal axis 110 and extend along the longitudinal axis 108 and terminate at any position on the shaft portion 102. As such, the bulbous portion 114 may include any suitable height or length. The bulbous portion 114, in some embodiments, may include a height or length that allows the bulbous portion 114 to engage a looped portion of another implant device (e.g., looped portion 214 of implant device 200A, 200B, and 200C in FIGS. 2A, 2B, and 2C, respectively) to lock implant device 100 to the other implant device, as discussed elsewhere herein (see e.g., FIGS. 3A and/or 3B).

In various embodiments, the looped portion 114 may include any suitable shape that is capable of being engaged with the looped portion of another implant device (e.g., the looped portion 214). In other words, the bulbous portion 114 can include any shape that complements and/or corresponds to the looped portion of the other implant device. Non-limiting examples of a shape suitable for the bulbous portion 114 may include, but are not limited to, a circle, an oval, and/or any other circular shape, etc., among other example shapes.

Alternatively, or additionally, the shape of the bulbous portion 114 may, in various embodiments, include a suitable amount of tapering. In some embodiments, the tapering may originate at a crown 118 of the bulbous portion 114 that is located beginning at the first terminal axis 110 and continually taper down along the longitudinal axis 108 to a foot 120 of the bulbous portion 114. In further embodiments, the tapering may originate at the crown 118 and terminate a position that is away from the foot 120 or the tapering may originate at a position that is away from the crown 118 and continually taper down along the longitudinal axis 108 to the foot 120 such that the bulbous portion 114 can include a tapered portion and a non-tapered portion. In alternative embodiments, the tapering may originate at a position that is away from the crown 118 and terminate at a position that is away from the foot 120 such that the bulbous portion 114 can include a tapered portion and multiple non-tapered portions.

In various embodiments, a tapered portion of the bulbous portion 114 may include any suitable type of tapering that is known or developed in the future and is capable of creating a force or compression, in any desired amount, when engaged and/or connected with another implant device (e.g., implant device 200A, 200B, and 200C in FIGS. 2A, 2B, and 2C, respectively), as discussed elsewhere herein. In some embodiments, the taper in the bulbous portion 114 may comprise a Morse-taper.

A bulbous portion 114 may include a thread 122 located on its external surface that rotates in a helix along a rotational axis 124 of the bulbous portion 114 and down the longitudinal axis 108. The thread 122, in various embodiments, may rotate in the range of about ten degrees (10°) to three hundred sixty degrees (360°), among other examples. In some embodiments, the thread 122 may rotate 360° along the rotational axis 124. In further embodiments, the thread 122 may rotate less than 360° along the rotational axis 124. In an example embodiment, the thread 122 rotates ninety degrees (90°) along the rotational axis 124. Various embodiments of the thread 122 can be considered a single-thread since they rotate less than or equal to 360° along the rotational axis 124.

In various embodiments, the thread 122 may rotate at any suitable angle along the rotational axis 124. In some embodiments, the thread 122 may rotate at an angle to create a spaced apart or wide thread along the longitudinal axis 108, while in other embodiments the thread 122 may rotate at an angle to create a tight or narrow thread along the longitudinal axis 108. In further embodiments, the thread 122 can rotate at the same angle and/or an angle that corresponds to an angle at which a groove on an interior surface of a looped portion (e.g., groove 222 on looped portion 214) rotates such that the thread 122 and the groove lock the bulbous portion 114 and the looped portion together when engaged, as discussed elsewhere herein (e.g., FIGS. 3A and/or 3B).

The thread 122 may include any suitable height and/or shape that can allow the thread 122 to engage a groove or other thread. In various embodiments, the thread 122 may include any suitable height and/or shape that may be compatible with and/or may correspond to a depth and/or shape of a groove (e.g., groove 222) that can allow the bulbous portion 114 to be locked with a looped portion (e.g., looped portion 214 in FIGS. 2A, 2B, and 2C) such that implant device 100 can form a portion of an implant assembly (e.g., implant assembly 300A in FIGS. 3A and/or 3B) along with at least one other implant device (e.g., implant device 200A, 200B, and 200C in FIGS. 2A, 2B, and 2C, respectively), as discussed elsewhere herein (e.g., FIGS. 3A and/or 3B).

In further embodiments, the thread 122 may include a sufficient amount of height such that the thread 122 can be considered a wing. In some embodiments, the thread 122 may include a height in the range of about 0.5 mm to about 2 mm, although other heights are possible and contemplated herein.

Further, the thread 122 can originate and/or terminate at any suitable location on the bulbous portion 114. In various embodiments, the thread 122 may originate at a position along the crown 118 of the bulbous portion 114, may terminate at a position along the foot 120 of the bulbous portion 114, may originate at a position along the crown 118 and terminate at a position along the foot 120, or may originate at a position that is away from the crown 118 and terminate at a position that is away from the foot 120.

The bulbous portion 114, in some embodiments, may include one or more additional threads 122 such that the bulbous portion 114 can include multiple single-threads. For instance, the threads 122 may be spaced apart such that no single-thread 122 includes greater than 360° of rotation along the rotational axis 124. In some aspects, two or more single-threads 122 may may rotate in parallel or not in parallel in relation to one another. In further aspects, two or more single-threads 122 may originate at the same location (e.g., crown 118) or different locations on the bulbous portion 114 and/or terminate at the same location (e.g., foot 120) or different locations on the bulbous portion 114. For instance, two or more threads 122 may originate at the crown 118 of the bulbous portion 114, one thread 122 may originate at the crown 118 and a second thread 122 may terminate at the foot 120 of the bulbous portion, two or more threads 122 may terminate at the foot 120, two or more threads 122 may originate at the crown 118 and terminate at the foot 120, or two or more threads 122 may both originate and terminate at different locations on the bulbous portion 114, etc., among other location combinations that are possible and contemplated herein.

Figure 2A:
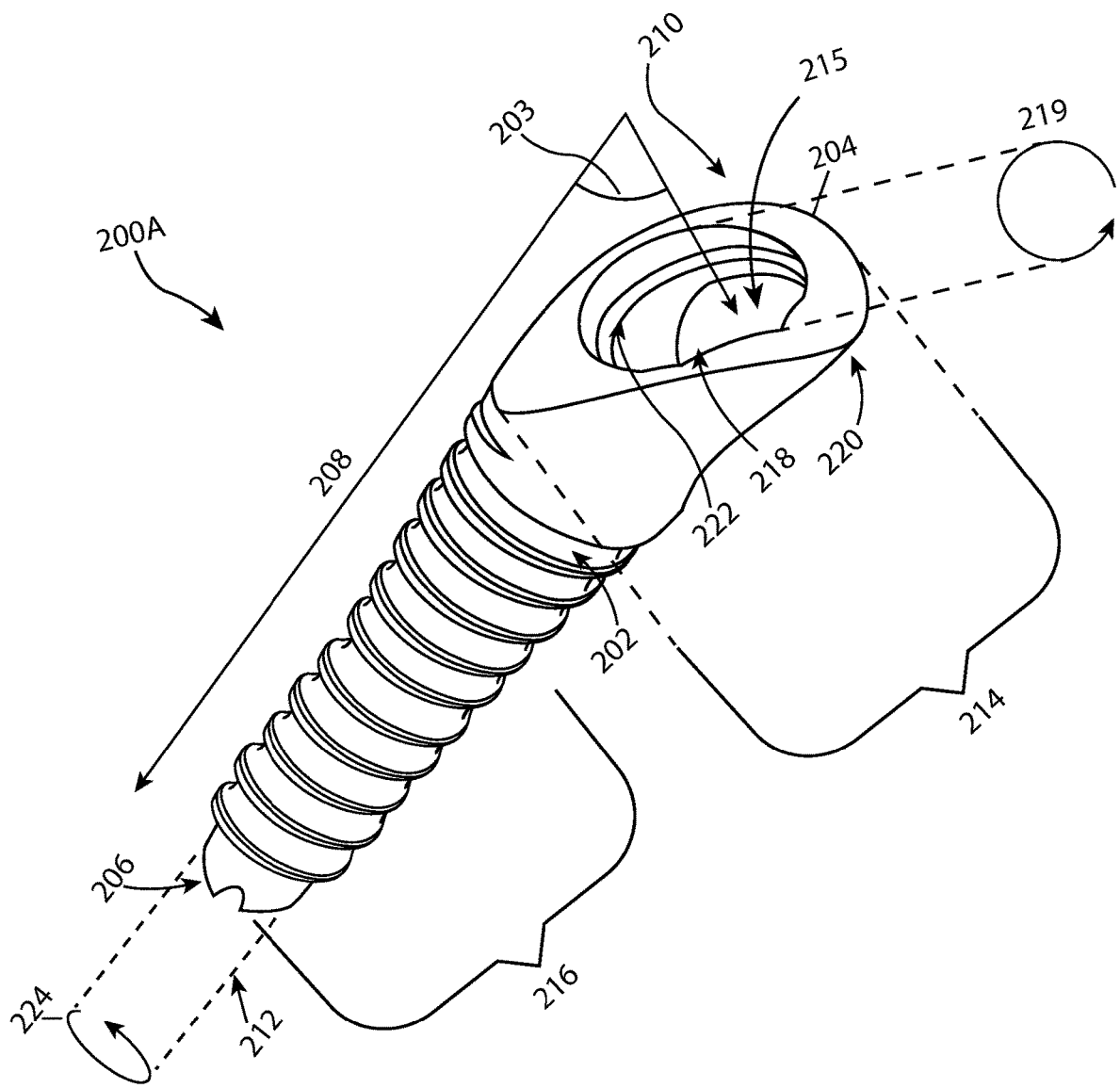
FIG. 2A is a diagram illustrating one embodiment of another implant device that can be engaged with the implant device of FIG. 1 to create an implant assembly.
Figure 2B:
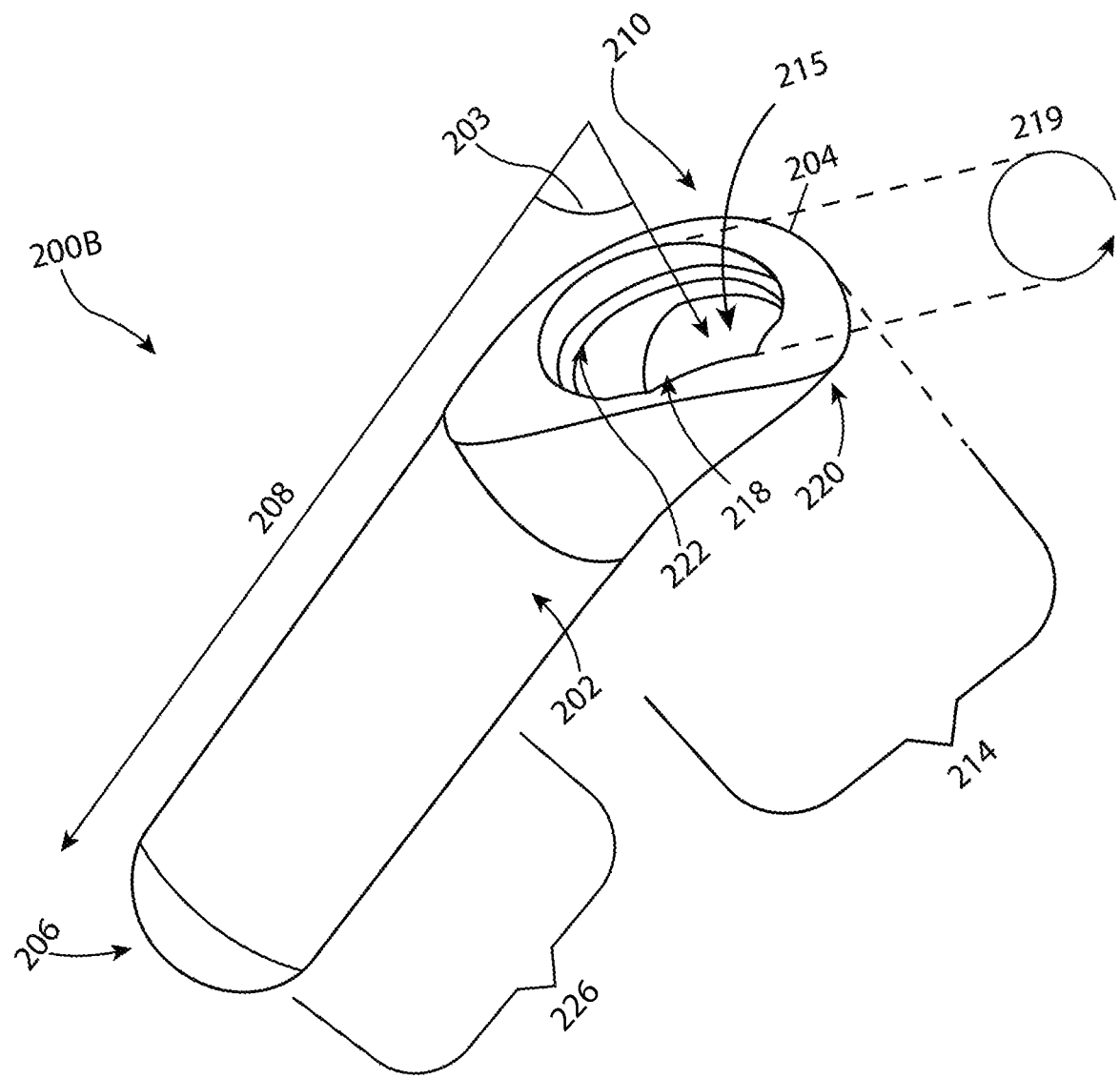
FIG. 2B is a diagram illustrating another embodiment of the other implant device.
Figure 2C:
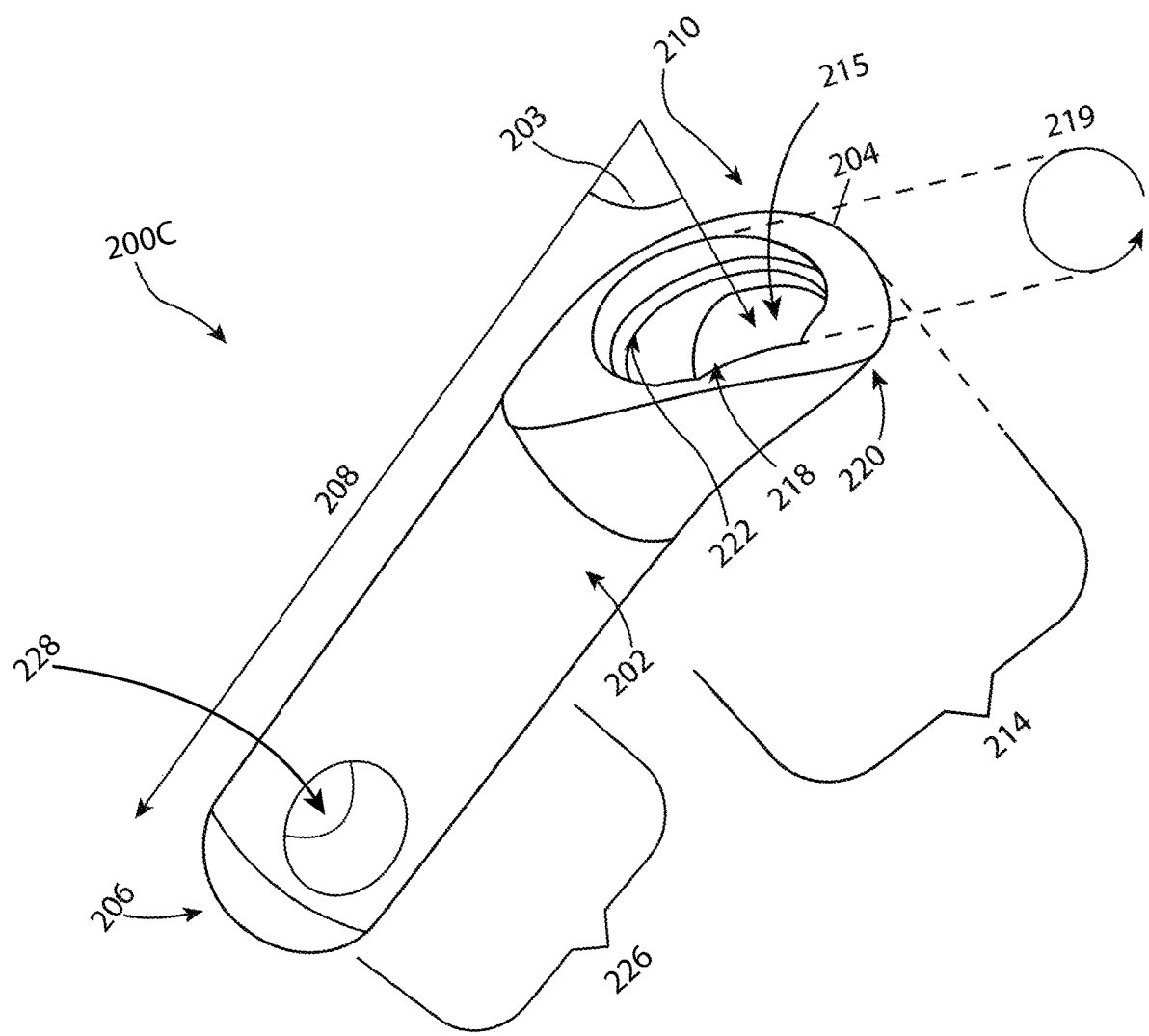
FIG. 2C is a diagram illustrating yet another embodiment of the other implant device.

The crown 118 of the bulbous portion 114, in various embodiments, may include a mechanism 126 that can be engaged by a tool that allows the implant device 100 to be implanted into a bone or joint and/or engaged with a looped portion of another implant device (e.g., looped portion 214 of implant device 200A, 200B, and 200C in FIGS. 2A, 2B, and 2C, respectively). In some embodiments, the mechanism 126 may include characteristics similar to an aperture in the head of a screw (e.g., a Phillips screw, flat-head screw, star screw, box screw, hex screw, etc., among other examples) that can allow a screwdriver, Allen wrench, hex key, rotational tool, or similar tool, etc. to engage the aperture 126.

The second end 106, in various embodiments, may include a screw portion 116 on the shaft portion 102 that extends along the longitudinal axis 108 and terminates at the second terminal axis 112. The screw portion 116 may be any suitable length that allows the implant device 100 to be implanted into a bone or joint. Further, the screw portion 116 may be tapered in any suitable manner that is known or developed in the future that is capable of allowing the implant device 100 to be implanted into a bone or joint. The screw portion 116 may further include a plurality of threads 128 including any suitable height, any suitable width, and/or suitable amount of space between each thread 128. For instance, the plurality of threads 128 may include any suitable number rotations or suitable amount of rotation along the rotational axis 124 that is greater than 360°.

The implant device 100 may comprise any material that is known or developed in the future that is capable of being implanted into a bone or joint. Non-limiting examples of suitable materials include, but are not limited to, a metal, an alloy, a composite material, and/or the like materials, etc., among other example materials. Some suitable specific non-limiting examples include titanium, stainless steel, nitinol, cobalt chromium, and/or aluminum, etc., among other suitable materials that are possible and contemplated herein.

In various embodiments, the implant device 100 may include any suitable shape that is capable of being implanted into a bone or joint. Non-limiting examples of a shape suitable for the implant device may include, but are not limited to, a circle, an oval, and/or any other circular shape, etc., among other example shapes.

Further, the implant device 100 may include any suitable length and/or suitable circumference that can allow the implant device 100 to be implanted into a bone or joint. A non-limiting example range of lengths includes, but is not limited to, about 10 mm to about 150 mm. Further, a non-limiting example range of circumferences includes, but is not limited to, about 2 mm to about 100 mm.

Referring now to FIG. 2A, FIG. 2A is a diagram illustrating an example implant device 200A in accordance with various embodiments. Implant device 200A may include a shaft portion 202 with a first end 204 and a second end 206 that are opposite one another along a longitudinal axis 208 and define a first terminal axis 210 and a second terminal axis 212, respectively. As shown, the implant device 200A may comprise, among other features, a looped portion 214 defining an aperture 215 at the first end 204 and a screw portion 216 at the second end 206. Although the various embodiments may be referred to herein as an implant device 200A, at least some embodiments of the implant device 200A may be considered and/or referred to as a post screw.

The looped portion 214, in various embodiments, may originate at the first terminal axis 210 and extend along the longitudinal axis 208 and terminate at any position on the shaft portion 202. As such, the looped portion 214 may include any suitable height or circumference. The looped portion 214, in some embodiments, may include a height or circumference that allows the looped portion 114 to engage a bulbous portion of another implant device (e.g., bulbous portion 114 of implant device 100) to lock implant device 200A to the other implant device, as discussed elsewhere herein (e.g., FIGS. 3A and/or 3B).

In various embodiments, the looped portion 214 may include any suitable shape that allows the bulbous portion of another implant device (e.g., bulbous portion 114) to be inserted through the aperture 215. In other words, the looped portion 214 can include any shape such that the aperture 215 complements and/or corresponds to the bulbous portion of the other implant device. Non-limiting examples of a shape suitable for the looped portion 214 may include, but are not limited to, a circle, an oval, and/or any other circular shape, etc., among other example shapes.

Alternatively, or additionally, the shape of the looped portion 214 may, in various embodiments, include a suitable amount of tapering on an interior surface that defines the aperture 215. In some embodiments, the tapering may originate at an insertion side 218 of the looped portion 214/aperture 215 that is located along a rotational axis 219. In further embodiments, the tapering may originate at the insertion side 218 and terminate at a position that is away from the exit side 220 or the tapering may originate at a position that is away from the insertion side 218 and continually taper down to the exit side 220 such that the interior surface can include a tapered portion and a non-tapered portion. In alternative embodiments, the tapering may originate at a position that is away from the insertions side 218 and terminate at a position that is away from the exit side 220 such that the interior surface of the looped portion 214 can include a tapered portion and multiple non-tapered portions.

In various embodiments, the interior surface of the looped portion 214 may be compatible with and/or correspond to any suitable type of tapering that is known or developed in the future and is capable of creating a force or compression, in any desired amount, when engaged and/or connected with a bulbous portion of another implant device (e.g., bulbous portion 114), as discussed elsewhere herein. In some embodiments, the interior surface of the looped portion 214 may be compatible with and/or correspond to a bulbous portion comprising a Morse-taper.

The aperture 215 may be created at an angle 203 with respect to the longitudinal axis 208 of the implant device 200A. The angle 203, in various embodiments, can be any suitable and/or desired angle in the range of about thirty degrees (30°) to about one hundred fifty degrees (150°), although other angles and/or ranges are possible and contemplated herein. In some embodiments, the angle 203 may be in the range of about 62 degrees (62°) to about 68 degrees (68°), among other example angles and/or ranges. In one embodiment, the angle 203 may be about sixty-five degrees (65°), among other possible angles that are contemplated herein.

The looped portion 214 may include a groove 222, which can also be considered a thread, which is located on its interior surface that is proximate to the aperture 215 and rotates in a helix along the rotational axis 219. The groove 222, in various embodiments, may rotate in the range of about ten 10° to 360°, among other examples. In some embodiments, the groove 222 may rotate 360° along the rotational axis 219. In further embodiments, the groove 222 may rotate less than 360° along the rotational axis 219. In an example embodiment, the groove 222 rotates 90° along the rotational axis 219. Various embodiments of the groove 222 can be considered a single-groove since they rotate less than or equal to 360° along the rotational axis 219.

In various embodiments, the groove 222 may rotate at any suitable angle along the rotational axis 219. In some embodiments, the groove 222 may rotate at an angle to create a spaced apart or wide groove, while in other embodiments the groove 222 may rotate at an angle to create a tight or narrow groove. In further embodiments, the groove 222 can rotate at the same angle and/or an angle that corresponds to an angle at which a thread on a bulbous portion (e.g., thread 122 on bulbous portion 114) rotates such that the groove 222 and the thread lock the bulbous portion and the looped portion 214 together when engaged, as discussed elsewhere herein (e.g., FIGS. 3A through 3D).

The groove 222 may include any suitable depth and/or shape that can allow the groove 222 to engage a thread. In various embodiments, the groove 222 may include any suitable depth and/or shape that may be compatible with and/or may correspond to a height and/or shape of a thread (e.g., thread 122) that can allow the looped portion 214 to be locked with a bulbous portion (e.g., bulbous portion 114) such that implant device 200A can form a portion of an implant assembly (e.g., implant assembly 300A in FIGS. 3A and/or 3B) along with at least one other implant device (e.g., implant device 100), as discussed elsewhere herein (e.g., FIGS. 3A and/or 3B). In some embodiments, the groove 222 may include a depth in the range of about 0.05 mm to about 6 mm, although other depths are possible and contemplated herein.

Further, the groove 222 can originate and/or terminate at any suitable location on the interior surface of the looped portion 214. In various embodiments, the groove 222 may originate at a position along the insertion side 218 of the looped portion 214, may terminate at a position along the exit side 220 of the looped portion 214, may originate at a position along the insertion side 218 and terminate at a position along the exit side 220, or may originate at a position that is away from the insertion side 218 and terminate at a position that is away from the exit side 220.

In some embodiments, the looped portion 214 may include one or more grooves 222 that can provide a self-correction mechanism when a single-thread (e.g., thread 122) engages the looped portion 214. For instance, the groove(s) 222 may be angled and/or positioned in a manner such that the insertion angle and/or trajectory of an implant device (e.g., implant device 100) into the aperture 215 can be automatically or a least semi-automatically modified as a thread (e.g., thread 122) of the implant device catches or engages a particular groove 222 to better ensure that the implant device is properly implanted and/or implanted on a proper angle/trajectory.

In some embodiments, the looped portion 214 may include one or more additional grooves 222 such that the looped portion 214 can provide multiple engagement points for a single-thread (e.g., thread 122). For instance, the grooves 222 may be spaced apart such that a single-thread has multiple locations or opportunities to catch or engage a groove 222. In some aspects, two or more single-grooves 222 may rotate in parallel or not in parallel in relation to one another. In further aspects, two or more single-grooves 222 may originate at different locations on the same rotational plane, different locations on different rotational planes, or the same location on different rotational planes, etc., among other examples that may provide multiple opportunities or chances for a single-thread (e.g., thread 122) to engage a groove 222 on the interior surface of the looped portion 214. The one or more additional grooves 222 in conjunction with the single-groove 222 that may provide multiple engagement points for a single-thread (e.g., thread 122), in some embodiments, can further provide a self-correction mechanism for inserting an implant device (e.g., implant device 100), as discussed elsewhere herein.

The looped portion 214, in further embodiments, may include one or more additional grooves 222 such that the looped portion 214 can accommodate multiple single-threads (e.g., single-threads 122). For instance, the grooves 222 may be spaced apart such that no single-groove 222 includes greater than 360° of rotation along the rotational axis 219. In some aspects, two or more single-grooves 222 may rotate in parallel or not in parallel in relation to one another. In further aspects, two or more single-grooves 222 may originate at the same location (e.g., a point of the looped portion 214 on/near the insertion side 218 or at an intermediary point between the insertion side and the exit side 220) or different locations on the looped portion 114 and/or terminate at the same location (e.g., a point of the looped portion 214 on/near the exit side 220 or at an intermediary point between the insertion side and the exit side 220) or different locations on the looped portion 214. For instance, two or more grooves 222 may originate at the insertion side 218 of the looped portion 214, one groove 222 may originate at the insertion side 218 and a second groove 222 may terminate at the exit side 220 of the looped portion 214, two or more grooves 222 may terminate at the exit side 220, two or more grooves 222 may originate at the insertion side 218 and terminate at the exit side 220, or two or more grooves 222 may both originate and terminate at different locations on the looped portion 214, etc., among other location combinations that are possible and contemplated herein. The one or more additional grooves 222 in conjunction with the single-groove 222 that can accommodate multiple single-threads (e.g., single-threads 122), in some embodiments, can further provide a self-correction mechanism for inserting an implant device (e.g., implant device 100), as discussed elsewhere herein.

The second end 206, in various embodiments, may include a screw portion 216 on the shaft portion 102 that rotates around a rotational axis 224 and extends along the longitudinal axis 208 and terminates at the second terminal axis 212. The screw portion 216 may be any suitable length that allows the implant device 200A to be implanted into a bone or joint. Further, the screw portion 216 may be tapered in any suitable manner that is known or developed in the future that is capable of allowing the implant device 200A to be implanted into a bone or joint. The screw portion 216 may further include a plurality of threads including any suitable height, any suitable width, and/or suitable amount of space between each thread. For instance, the plurality of threads may include any suitable number rotations or suitable amount of rotation along the rotational axis 224 that is greater than 360°.

The implant device 200A may comprise any material that is known or developed in the future that is capable of being implanted into a bone or joint. Non-limiting examples of suitable materials include, but are not limited to, a metal (e.g., aluminum), an alloy, a composite material, and/or the like materials, etc., among other example materials. Some suitable specific non-limiting examples include titanium, stainless steel, nitinol, cobalt chromium, and/or aluminum, etc., among other suitable materials that are possible and contemplated herein.

In various embodiments, the implant device 200A may include any suitable shape that is capable of being implanted into a bone or joint. Non-limiting examples of a shape suitable for the implant device may include, but are not limited to, a circle, an oval, and/or any other circular shape, etc., among other example shapes.

Further, the implant device 200A may include any suitable length and/or suitable circumference that can allow the implant device 200A to be implanted into a bone or joint. A non-limiting example range of lengths includes, but is not limited to, about 5 mm to about 150 mm. Further, a non-limiting example range of circumferences includes, but is not limited to, about 4 mm to about 50 mm.

With reference to FIG. 2B, FIG. 2B is a diagram illustrating an example implant device 200B in accordance with various embodiments. Implant device 200B may include a shaft portion 202 with a first end 204 including a looped portion 214 defining an aperture 215 and further including a second end 206 similar to the implant device 200A, as discussed elsewhere herein. As shown, the implant device 200B may further comprise, among other features, a smooth, substantially smooth, or nail portion 226 at the second end 206. The nail portion 226 is smooth or substantially smooth in that the nail portion 226 does include the threaded portion 216 of the implant device 200A. The nail portion 226 may include any suitable tip and/or construction that allows the implant device 220B to be tapped, struck, driven, hammered, nailed, pounded, and/or otherwise similarly inserted into and/or attached to a bone. Although the various embodiments may be referred to herein as an implant device 200B, at least some embodiments of the implant device 200B may be considered and/or referred to as a post screw.

Referring to FIG. 2C, FIG. 2C is a diagram illustrating an example implant device 200C in accordance with various embodiments. Implant device 200C may include a shaft portion 202 with a first end 204 including a looped portion 214 defining an aperture 215 and a second end 206 with a nail portion 226 similar to the implant device 200B, as discussed elsewhere herein. As shown, the implant device 200C may further comprise, among other features, an aperture 228 in the nail portion 226 at the second end 206.

The aperture 228 may include any suitable shape that can allow and/or enable the implant device 200C to be better secured into a bone. Similarly, the aperture 228 may include any suitable dimensions (e.g., length, width, volume, height, circumference, etc.) that can allow and/or enable the implant device 200C to be better secured into a bone. Although the various embodiments may be referred to herein as an implant device 200C, at least some embodiments of the implant device 200C may be considered and/or referred to as a post screw.

Figure 3A:
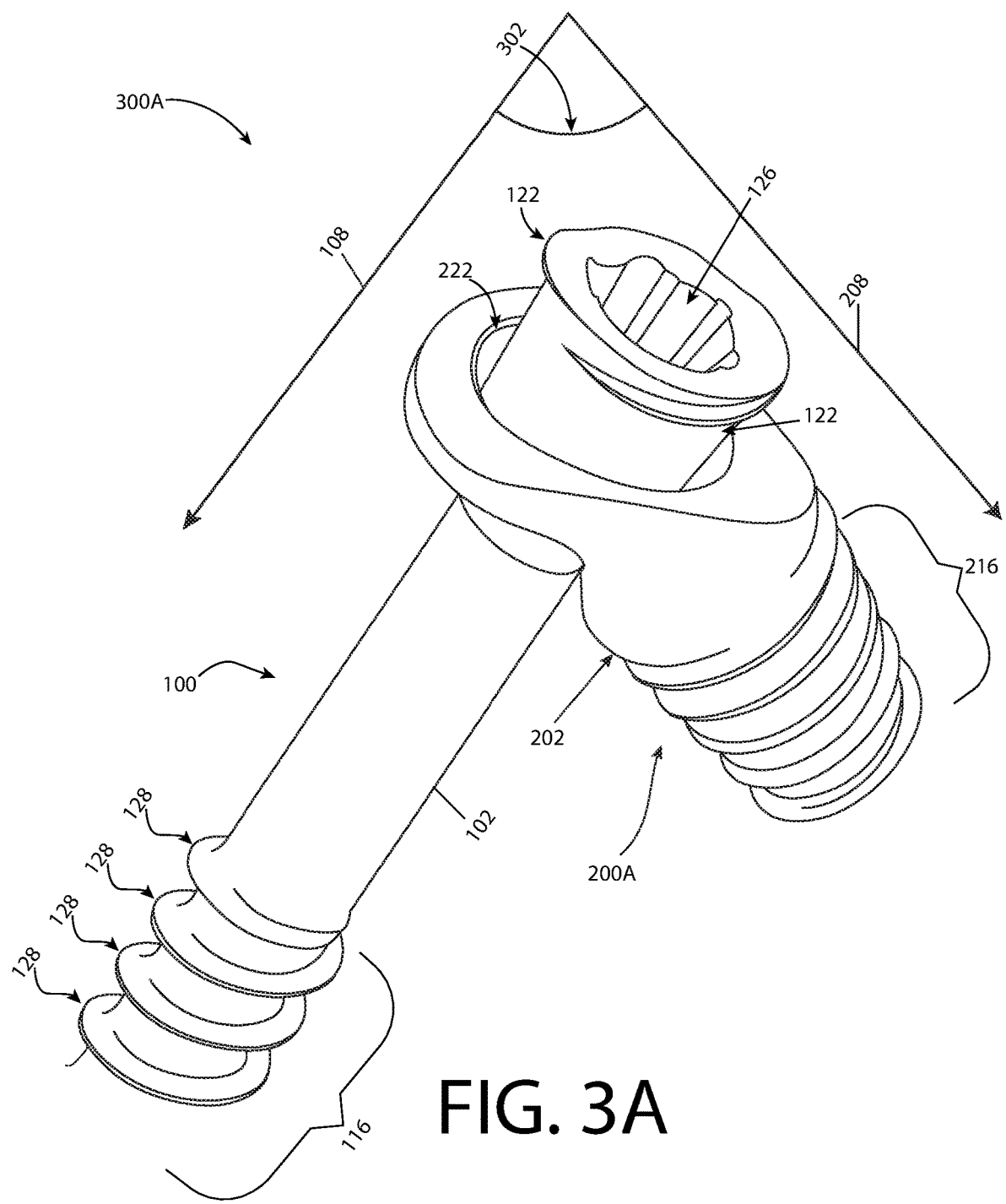
FIG. 3A is a diagram illustrating an anteroposterior view of an example implant assembly including the implant device of FIG. 1 and the implant device of FIG. 2A.
Figure 3B:
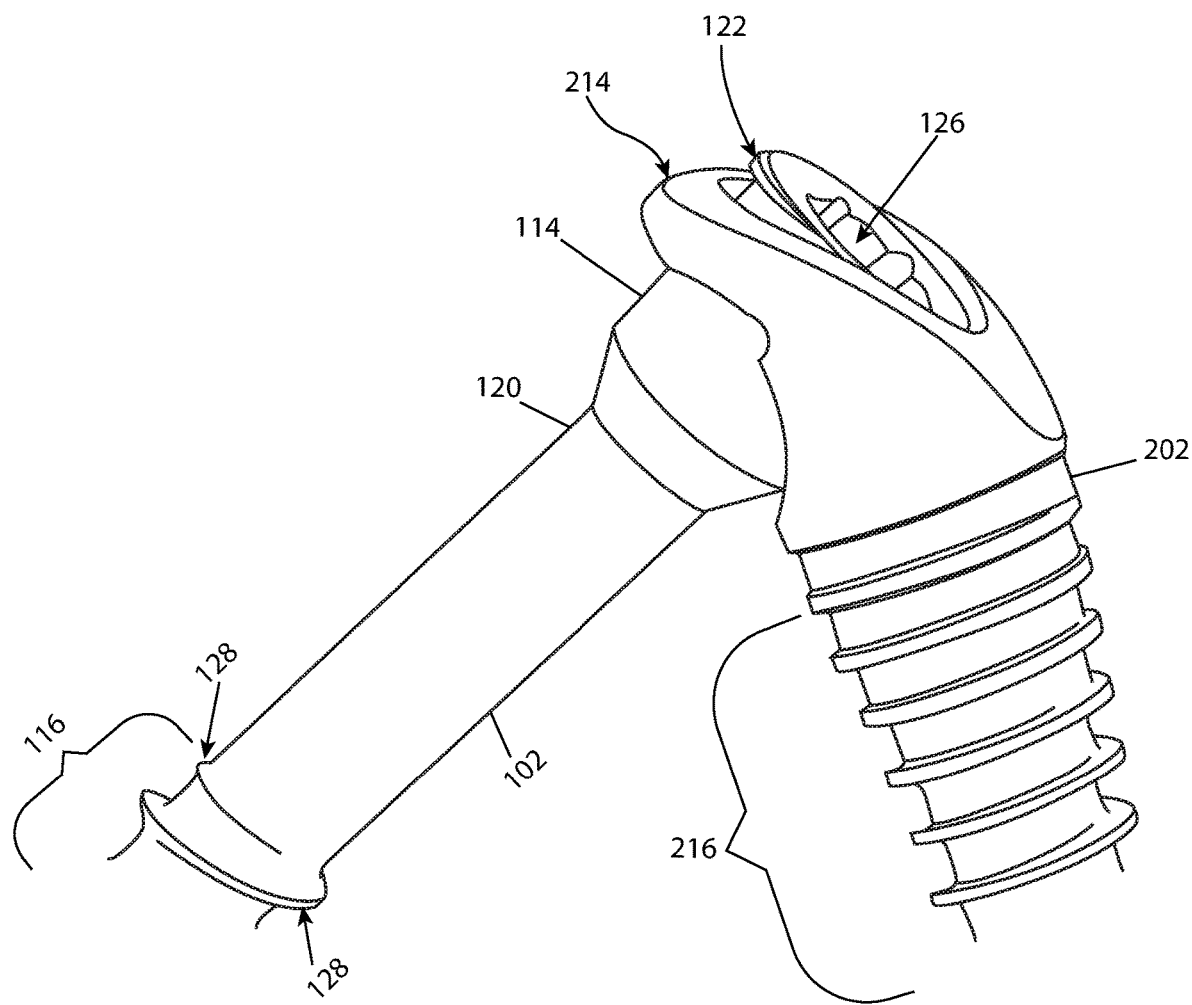
FIG. 3B is a diagram illustrating a lateral view of the example implant assembly of FIG. 3A.

With reference now to FIGS. 3A and 3B, FIGS. 3A and 3B illustrate an anteroposterior view and a lateral view, respectively, of an example implant assembly 300A in accordance with various embodiments. As shown, implant assembly 300A can comprise implant device 100 and implant device 200A.

In some embodiments, implant device 100 and implant device 200A may comprise the same material. In further embodiments, implant device 100 and implant device 200A can comprise different materials.

In accordance with various embodiments of implant assembly 300A, the implant device 200A may be initially implanted into a bone or a joint during use. For instance, the screw portion 216 of the implant device 200A may be implanted or screwed into a bone or joint using an implant tool, as discussed elsewhere herein.

Further, the implant device 100 may subsequently be inserted through aperture 215, the screw portion 116 first, until the bulbous portion 214 is seated inside the aperture 215. Once seated within the aperture 215, the implant device 100 may be rotated by inserting an appropriate tool, as discussed elsewhere herein, inside the mechanism 126 and rotating or twisting the tool so that the thread 122 or threads 122 engage and couple to the groove 222 and/or grooves 222.

The implant device 100 may be rotated until the bulbous portion 114 is sufficiently coupled to the looped portion 214 of the implant device 214 and/or a last thread 128 in the plurality threads 128 of the screw portion 116 that is capable of engaging a bone/joint is engaged (e.g., is screwed into the bone/joint), the screw(s) 122 of the implant device 100 may be engaged with the grove(s) 222 of the implant device 200A to lock or couple implant devices 100 and 200A together. A last thread in the plurality threads 128 of the screw portion 116 that is capable of engaging a bone/joint may be the thread that is farthest from the second end 206 and/or the second terminal axis 212 of implant device 200A or may be any other thread in the plurality threads 128.

In various embodiments, implant devices 100 and 200A may be implanted or screwed into the same bone or joint, different bones or joints, or in a bone and a joint, as needed or desired. In some embodiments, a self-correcting mechanism in the looped portion 214, as discussed elsewhere herein, may assist in ensuring that the implant device 100 is inserted through aperture 215 and implanted or screwed into the bone or joint at the proper angle and/or trajectory.

An angle 302 may be created between the horizontal axis 108 of the implant device 100 and the horizontal axis 208 of the implant device 200A when the single-thread(s) 122 and the single-groove(s) 222 are engaged with one another. The angle 302, in various embodiments, can be any suitable and/or desired angle in the range of about 30° to about 150°, although other angles and/or ranges are possible and contemplated herein. In some embodiments, the angle 302 may be in the range of about 62° to about 68°, among other example angles and/or ranges. In one embodiment, the angle 302 may be about 65°, among other possible angles that are contemplated herein.

While the use of a standard thread-groove screw engagement has been described in various embodiments herein, a reverse thread-groove screw engagement may be possible and is contemplated herein for various embodiments. For instance, the single-thread(s) 122 in the implant device 100 and the single-groove(s) 222 in the implant device 200A, in some embodiments, may be reverse threaded and correspond to one another. In further embodiments, the plurality of threads 128 in the implant device 100 and/or the plurality of threads in the implant device 200A may be reverse threaded.

A single-thread/single-groove screw engagement utilizing, for example, a single-thread 122 and a single-groove 222 can allow the implant devices 100 and 220 to be more easily engaged, locked, and/or coupled to one another, can allow the implant devices 100 and 220 to be more accurately engaged, locked, and/or coupled to one another, can be more efficient, can require less work, and/or can provide a stronger, more stable, and/or more secure locking connection than other technologies and/or techniques. Further, a single-thread/multi-groove engagement using, for example, a single-thread 122 and multiple single-grooves 222 can provide similar benefits as a single-thread/single-groove engagement and may provide one or more added features and/or one or more further improvements. In addition, multi-single-thread/multi-single-groove engagements using, for example, multiple single-threads 122 and multiple single-grooves 222 can provide similar benefits as a single-thread/single-groove engagement and/or a single-thread/multi-groove engagement and may provide one or more added features and/or one or more further improvements.

Figure 3C:
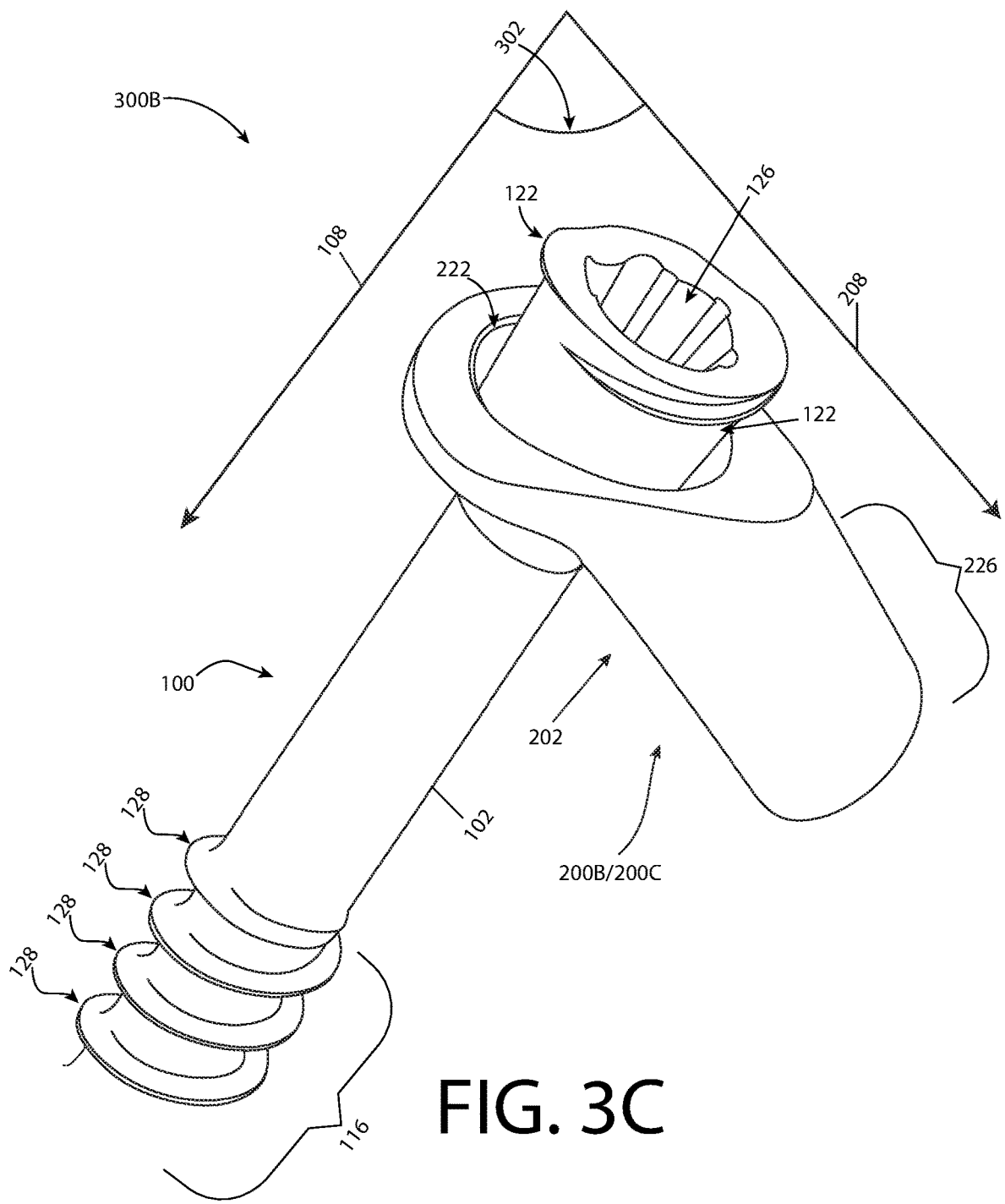
FIG. 3C is a diagram illustrating an anteroposterior view of another example implant assembly including the implant device of FIG. 1 and the implant device of FIG. 2B or 2C.
Figure 3D:
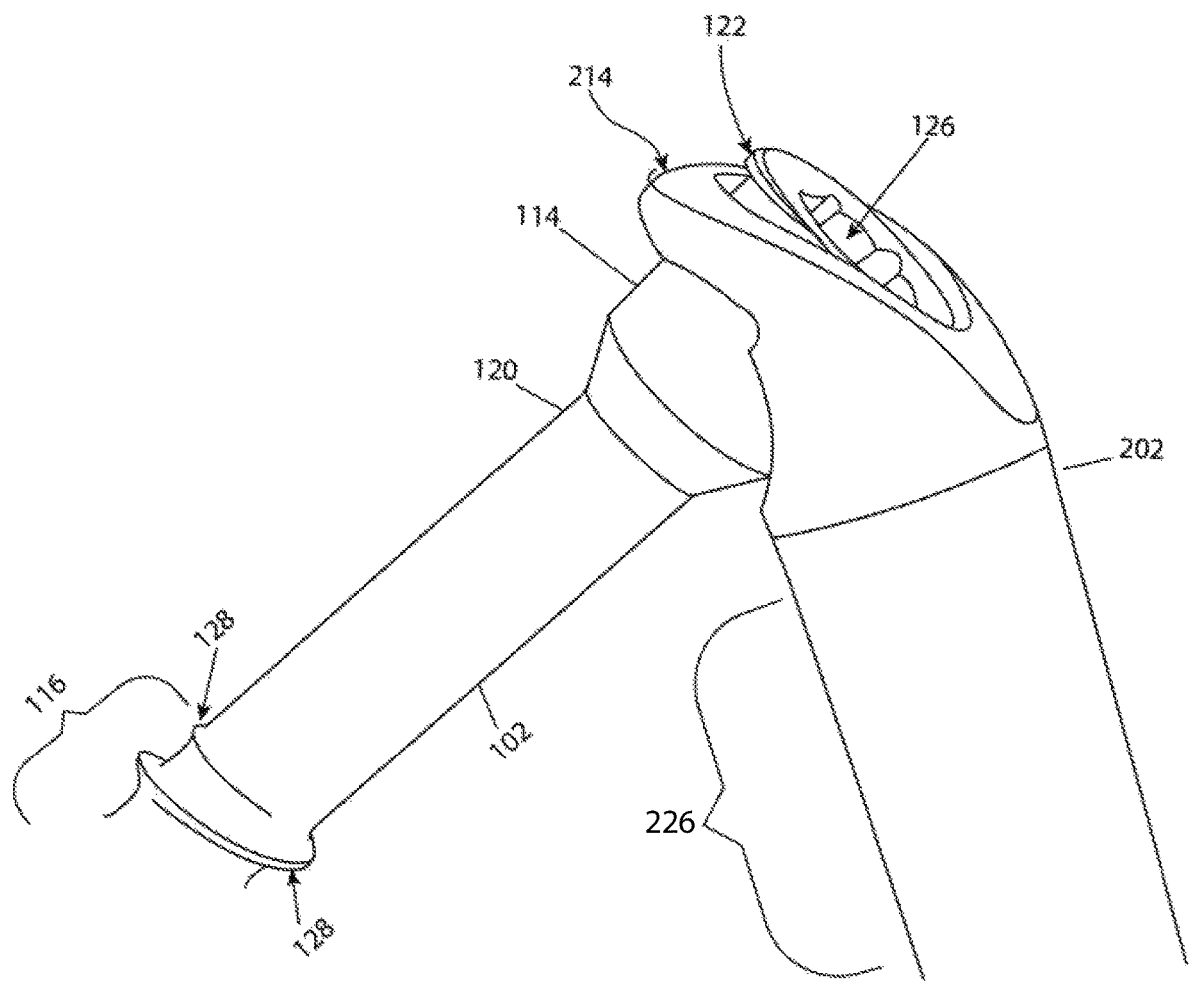
FIG. 3D is a diagram illustrating a lateral view of the example implant assembly of FIG. 3C.

Referring now to FIGS. 3C and 3D, FIGS. 3C and 3D illustrate an anteroposterior view and a lateral view, respectively, of an example implant assembly 300B in accordance with various embodiments. As shown, implant assembly 300B can comprise implant device 100 and implant device 200B or 200C.

In the various embodiments, the implant device 100 is implanted or screwed (via one or more threads 128 in the screw portion 116) into a bone and the implant device 200B or 200C is implanted or inserted (via the nail portion 226) into the same bone and/or a different bone as the implant device 100. The implant device 100 and the implant device 200B or 200C may be engaged with one another using any of the techniques discussed elsewhere herein. Further, the implant assembly 300B may be implanted into one or more bones and/or tissue and/or utilized similar to the implant assembly 300A, as discussed elsewhere herein.

The embodiments may be practiced in other specific forms. The described embodiments are to be considered in all respects only as illustrative and not restrictive. The scope of the technology is, therefore, indicated by the appended claims rather than by the foregoing description. All changes which come within the meaning and range of equivalency of the claims are to be embraced within their scope.

The invention claimed is:

1. An implant assembly, comprising: a first implant device including: a first end and a second end oppositely located along a longitudinal first axis, a bulbous portion at the first end that extends along the first axis, the bulbous portion comprising: a crown defining a first terminal axis of the first end, and a thread disposed on an exterior surface of the bulbous portion and originating at the crown, and first threaded portion at the second end that extends along the first axis and defining a second terminal axis; and a second implant device including: a third end and a fourth end oppositely located along a longitudinal second axis, and a looped portion defining an aperture at the third end and including an interior surface with a groove disposed therein, wherein: the thread and the groove lock the bulbous portion and the looped portion when engaged, and the looped portion defining the aperture provides an insertion side and an exit side for the first implant device.

2. The implant assembly of claim 1, wherein the thread is a single-thread.

3. The implant assembly of claim 2, wherein the groove is a single-groove.

4. The implant assembly of claim 1, wherein the groove is a single-groove.

5. The implant assembly of claim 1, wherein the thread rotates 360 degrees around the bulbous portion along the first axis.

6. The implant assembly of claim 5, wherein the groove rotates 360 degrees around the interior surface of the looped portion.

7. The implant assembly of claim 1, wherein the groove rotates 360 degrees around the interior surface of the looped portion.

8. The implant assembly of claim 1, wherein the thread rotates less than 360 degrees around the bulbous portion along the first axis.

9. The implant assembly of claim 8, wherein the groove rotates less than 360 degrees around the interior surface of the looped portion.

10. The implant assembly of claim 1, wherein the groove rotates less than 360 degrees around the interior surface of the looped portion.

11. The implant assembly of claim 1, wherein at least one of:
the groove terminates at the exit side; and
the groove originates at the insertion side.

12. The implant assembly of claim 11, wherein the fourth end comprises a nail portion.

13. The implant assembly of claim 1, wherein the fourth end comprises a screw portion.

14. An implant device system, comprising: an implant device, comprising: a first end and a second end oppositely located along a longitudinal axis, a bulbous portion at the first end that extends along the longitudinal axis, the bulbous portion comprising: a crown defining a first terminal axis of the first end, and a thread disposed on an exterior surface of the bulbous portion and originating at the crown, and a threaded portion at the second end that extends along the longitudinal axis and defining a second terminal axis; and an external implant device comprising: a looped portion defining an aperture, and a groove in the looped portion defining the aperture, wherein: the threaded portion is configured to implant in a bone, the implant device is configured to couple to the external implant device, the thread is configured to engage with the groove in the looped portion defining the aperture of the external implant device to lock the bulbous portion of the implant device and the looped portion defining the aperture of the external implant device, and the looped portion defining the aperture provides an insertion side and an exit side for the implant device in coupling the implant device and the external implant device.

15. The implant device of claim 14, wherein the thread is a single-thread.

16. The implant device of claim 14, wherein the thread rotates less than or equal to 360 degrees around the bulbous portion along the longitudinal axis.

17. An implant device system, comprising: an implant device, comprising: a first end and a second end oppositely located along a longitudinal axis, and a looped portion defining an aperture at a first terminal axis of the first end and including an interior surface with a groove disposed therein; and an external implant device comprising a bulbous portion including a crown and a thread disposed on an exterior surface of the bulbous portion and originating at the crown, wherein: the implant device is configured to couple to the external implant device, the groove in the looped portion defining the aperture is configured to engage with the thread on the exterior surface of the bulbous portion of the external implant device to lock the looped portion of the implant device and the bulbous portion of the external implant device, and the looped portion defining the aperture provides an insertion side and an exit side for the external implant device in coupling the implant device and the external implant device.

18. The implant device of claim 17, wherein the groove is a single-groove that rotates less than or equal to 360 degrees around the interior surface of the looped portion defining the aperture.

19. The implant device of claim 17, wherein the second end comprises one of a screw portion and a nail portion configured to implant in a bone.

20. The implant system of claim 17, wherein: the groove is a single-groove; the groove rotates less than 360 degrees around the interior surface of the looped portion; the thread is a single thread; and the thread rotates less than 360 degrees around the bulbous portion.

* * * * *